United States Patent [19]

Rajagopalan

[11] Patent Number: 5,602,236
[45] Date of Patent: Feb. 11, 1997

[54] METAL-CONTAINING STEROID MIMICS AND LIGANDS USEFUL IN THE PREPARATION THEREOF

[75] Inventor: Raghavan Rajagopalan, Maryland Heights, Mo.

[73] Assignee: Mallinckrodt Medical, Inc., St. Louis, Mo.

[21] Appl. No.: 224,928

[22] Filed: Apr. 8, 1994

[51] Int. Cl.[6] .............................. C07F 5/00; C07F 13/00; C07J 73/00

[52] U.S. Cl. .................. 534/10; 534/14; 534/15; 534/16; 544/4; 544/47; 544/49; 544/225; 544/237; 546/141; 546/142; 546/146; 546/147; 546/150; 546/4; 540/3

[58] Field of Search .................. 424/1.45, 1.65, 424/9.361; 540/2, 3; 534/10, 14, 15, 16; 544/4, 47, 49, 225, 237; 546/141, 142, 146, 147, 150

[56] References Cited

U.S. PATENT DOCUMENTS

| | | | |
|---|---|---|---|
| 3,492,293 | 1/1970 | Fried | 260/239.55 |
| 4,030,886 | 6/1977 | Bayly et al. | 23/230.6 |
| 4,083,947 | 4/1978 | Monks et al. | 424/1 |
| 4,171,351 | 10/1979 | Van der Veek | 424/1 |
| 4,202,876 | 5/1980 | Monks et al. | 424/1.5 |
| 4,879,379 | 11/1989 | Kidani | 540/3 |
| 4,983,646 | 1/1991 | Jaouen et al. | 552/630 |
| 5,330,737 | 7/1994 | Rajagopalan | 424/1.65 |

OTHER PUBLICATIONS

Chi, et al., J. Med. Chem., vol. 37, No. 7 (1994) "Homodimeric and Heterodimeric Bis(amino thiol) Oxometal Complexes with Rhenium (V) and Technetium (V). Control of Heterodimeric Complex Formation and an Approach to Metal Complexes that Mimic Steroid Hormones", pp. 928–937.

Top, et al., J. Chem Soc., Chem., (1993) "Synthetic Strategy for Organometallic Complexes of Rhenium with Exceptionally High Affinity for the Oestradiol Receptor"; their Potential Use as Imaging and Therapeutic Agents, pp. 453–454.

Chi et al., J., Am. Chem. Soc., vol. 115, No. 15, (1993) "Selective Formation of Heterodimeric Bis–Bidentate Aminothiol–Oxometal Complexes of Rhenium (V)", pp. 7045–7046, see Scheme 1.

Donegan, Cancer Supplement, vol. 70, No. 6 (1992) "Prognostic Factors: Stage and Receptor Status in Breast Cancer", pp. 1755–1764.

Rayter, Br. J. Surg., vol. 78, No. 5 (1991) "Steroid receptors in breast cancer".

Wilding, Cancer Surveys, vol. 14: Growth Regulation by Nuclear Hormone Receptors (1992) "The Importance of Steroid Hormones in Prostate Cancer", pp. 113–130.

King, J. Steroid Biiochem. Molec. Biol., vol. 39, No. 5B (1991) "A Discussion of the Roles of Oestrogen and Progestin in Human Mammary Carcinogenesis", pp. 811–818.

Labrie, Endocrinology and Metabolism Clinics of North America, vol. 20, No. 4 (1991), "Endocrine Therapy for Prostate Cancer", pp. 845–872.

DE 4,104,257 as abstracted in CA 118:6878, 1992.
DE 3,827,727 as abstracted in CA 113:132024, 1990.

*Primary Examiner*—John Kight
*Assistant Examiner*—Lara E. Chapman
*Attorney, Agent, or Firm*—Thomas P. McBride

[57] ABSTRACT

Metal-containing steroid mimic complexes are provided. Compositions containing a metal ion incorporated into a steroid skeleton structure and ligands useful in the preparation of such compositions are also provided. The metal ion is preferably a radionuclide, such as technetium, rhenium or gallium. Methods for using the metal complexes for diagnostic and therapeutic purposes are further provided.

16 Claims, 2 Drawing Sheets

METAL-CONTAINING STEROID MIMICS AND LIGANDS USEFUL IN THE PREPARATION THEREOF

BACKGROUND OF THE INVENTION

1. Field of the Invention

This invention relates in general to metal-containing compositions which mimic the skeletal structure of asteroid, and more particularly to such compositions in which a selected metal ion is integrated into a tertiary or quaternary center of a steroid skeleton structure by occupying a position in the steroid structure previously occupied by a carbon atom and which are useful in delivering a metal to a targeted site for diagnostic or therapeutic purposes.

2. Description of Background Art

The development of radiopharmaceuticals capable of delivering a selected metal ion to a targeted biological site has been the focus of much research in the biological and medical fields. Radiopharmaceuticals have, in fact, been developed that are capable of being targeted to a specific site and have found use in radioimaging, radiotherapy, and as a tool for the prognosis of disease. In recent years the use of radiopharmaceuticals to diagnose, image and/or provide therapy for tumors has been increasing. Recent studies have also shown that steroid receptors in tumor cells, such as those found in breast cancer and prostate cancer, may provide important prognostic information on the status of the tumor and in selecting an effective course of treatment. Rayter, Z., "Steroid Receptors in breast cancer," *Br. J. Surg.* (1991) Vol. 78, pp.528–535; Donegan, W. L., "Prognostic Factors," *Cancer Supplement* (1992) Vol. 70, No. 6, pp. 1755–1764; Wilding, G., "The Importance of Steroid Hormones in Prostate Cancer," *Cancer Surveys Volume 14: Growth Regulation by Nuclear Hormone Receptors*, (1992) pp.113–130. It would be considered an advance in the art if a radiopharmaceutical that could advantageously exploit the presence of steroid receptors on a tumor cell or other biological tissue were available.

One method by which steroid receptors on tumors or other biological tissues could be utilized would be to attach a radiolabelled metal complex to the steroid molecule which binds to the receptor. Various effector molecules, such as drugs, enzymes, chemotoxins, probes, and the like, have been prepared for targeted delivery to a biological site bycovalently attaching a receptor specific carrier molecule, such as an antibody or a peptide, thereto. Halpern et al., *Diagnostic Imaging,* 1983, 40; Hnatowich et al., *Science,* 1983, 220, 613. This approach has been referred to as an "external bifunctional" approach and has found some success. It has also been found, however, that if the carrier is a small molecule, i.e. one having a molecular weight of less than about 500 Daltons, the attachment of effector molecules often destroys the receptor binding capability of the carrier molecule. Steroids are small molecules, typically having a molecular weight of around 400 Daltons, and the covalent attachment of a radioactive metal complex to the steroid may obstruct the ability of the steroid to bind to the receptor. Thus, any steroid based radiopharmaceutical should be one that does not adversely affect the binding properties of the steroid. Moreover, an effective steroid-based radiopharmaceutical should maintain the relative size, shape and structure of the steroid molecule.

Others have attempted to prepare a radionuclide complex that is intended to mimic asteroid. In Chi and Katzenellenbogen, *J. Am. Chem. Soc.,* (1993) 115, pp. 7045–7046, heterodimeric bis-bidentate aminothiol complexes of technetiumand rhenium have been prepared that purportedly more closely resembled the size and shape of asteroid molecule. The complexes described by Chi and Katzenellenbogen do not, however, incorporate a radionuclide into the perhydrocyclopentanophenanthrene ring system of the typical steroid structure. Thus, the Chi and Katzenellenbogen approach is one that attempts to combine known ligands in a manner that approximates the size and shape of asteroid or other biomolecule, but that does not use the basic structure of the biomolecule as the template.

Another approach that has been utilized to provide biomolecule mimics is referred to as an "internal bifunctional" approach which incorporates the selected ion directly into the molecular framework of the carrier molecule in such a manner that the resulting structure will be topologically similar to the original molecule. This approach, which is primarily inspired by the fact that antibodies, enzymes, and receptors are multispecific, has been used to prepare opiate alkaloid mimics and is described in my co-pending U.S. application filed on Dec. 6, 1991 having Ser. No. 07/804, 852, now U.S. Pat. No. 5,330,737, the entirety of which is herein incorporated by reference hereto. Heretofore, however, the use of an internal bifunctional approach for the preparation of steroid-based radiopharmaceuticals has not been disclosed or suggested. It would be desirable, therefore, to provide metal containing steroid mimics that incorporate a selected metal ion into the structure of a steroid by an internal bifunctional approach and ligands useful in the preparation of such steroid mimics.

SUMMARY OF THE INVENTION

The present invention is directed to a composition comprising a metal ion incorporated into a steroid skeleton structure and ligands useful in the preparation of such compositions. In particular, a composition comprised of a steroid skeleton structure having a metal ion at at least one of the tertiary or quaternary centers of the steroid skeleton structure and a donor atom capable of bonding to the metal ion at the positions in the steroid skeleton structure which are adjacent to the metal ion is provided. The metal ion is preferably a radionuclide useful in radioimaging or radiotherapy. The radionuclide is incorporated directly into the molecular framework of the steroid molecule in such a manner that the resulting composition is similar in size, shape and molecular topology to a non-modified steroid and retains the relative binding properties of a steroid molecule.

The present invention is further directed to ligands useful in preparing radionuclide compositions having the structure:

where $R^1$ and $R^2$ are the same or different and each is selected from the group consisting of hydrogen, hydroxyl, carboxyl, amino, alkyl, aryl, alkaryl, alkaroyl, hydroxyalkyl, hydroxyalkaroyl, alkoxy, alkoxycarbonyl and carbamoyl and where the carbon containing portions contain between 1 and 10 carbon atoms;

$R^3$, $R^4$ and $R^5$ are the same or different and each is selected from the group consisting of hydrogen, alkyl, hydroxyalkyl, aminoalkyl, carboxyalkyl or mercaptoalkyl and where the carbon containing portions contain between 1 and 6 carbon atoms;

$X^1$ is selected from the group consisting of —CH$_2$, —CHOH, —C=O, —CHCH$_2$SH, or —CHCO$_2$H; and $Y^1$ is selected from the group consisting of —SH, or —NR$^6$R$^7$, R$^6$ and R$^7$ being the same or different and are defined in the same manner as R$^1$ and R$^3$, respectively;

or a ligand having the structure:

II where R$^8$ and R$^9$ are the same or different and each is selected from the group consisting of hydrogen, hydroxyl, carboxyl, amino, alkyl, aryl, alkaryl, alkaroyl, hydroxyalkyl, hydroxyalkaryl, alkoxy, alkoxycarbonyl and carbamoyl and where the carbon containing portions contain between 1 and 10 carbon atoms;

R$^{10}$, R$^{11}$, and R$^{12}$ are the same or different and each is selected from the group consisting of hydrogen, alkyl, hydroxyalkyl, aminoalkyl, carboxyalkyl or mercaptoalkyl and where the carbon containing portions contain between 1 and 6 carbon atoms;

$X^2$ is selected from the group consisting of —SH and —NR$^{13}$R$^{14}$, R$^{13}$ and R$^{14}$ being the same or different and are defined in the same manner as R$^8$ and R$^{10}$, respectively; and $Z^1$ is selected from the group consisting of —CH$_2$, —CHOH, and —C=O.

The present invention is also directed to metal radionuclide complexes having the structure:

III where R$^{15}$ and R$^{16}$ are the same or different and each is selected from the group consisting of hydrogen, hydroxyl, carboxyl, amino, alkyl, aryl, alkaryl, alkaroyl, hydroxyalkyl, hydroxyalkyl, alkoxy, alkoxycarbonyl and carbamoyl and where the carbon containing portions contain between 1 and 10 carbon atoms;

R$^{17}$ is selected from the group consisting of hydrogen, alkyl, aryl, alkaryl, hydroxyalkyl, mercaptoalkyl, and alkoxyalkyl;

R$^{18}$ and R$^{19}$ are the same or different and each is selected from the group consisting of hydrogen, alkyl, hydroxyalkyl, aminoalkyl, carboxyalkyl or mercaptoalkyl and where the carbon containing portions contain between 1 and 6 carbon atoms;

$X^3$ is selected from the group consisting of —CH$_2$, —CHOH, —C=O, —CHCH$_2$SH, or —CHCO$_2$H;

$Y^3$ is selected from the group consisting of —S— and —NR$^{20}$R$^{21}$, where R$^{20}$ and R$^{21}$ are defined in the same manner as R$^{15}$ and R$^{18}$, respectively; and M$^1$ is selected from the group consisting of Technetium, Rhenium, Indium, Gallium, Cobalt, Copper, Yttrium, Terbium, Samarium, Holmium, Lutetium, Gadolinium, Manganese and Iron;

or a radionuclide complex having the structure:

IV where R$^{22}$ and R$^{23}$ are the same or different and each is selected from the group consisting of hydrogen, hydroxyl, carboxyl, amino, alkyl, aryl, alkaryl, alkaroyl, hydroxyalkyl, hydroxyalkaryl, alkoxy, alkoxycarbonyl and carbamoyl and where the carbon containing portions contain between 1 and 10 carbon atoms;

R$^{24}$ and R$^{25}$ is selected from the group consisting of hydrogen, alkyl, aryl, alkaryl, hydroxyalkyl and alkoxyalkyl;

R$^{26}$ is selected from the group consisting of hydrogen, alkyl, hydroxyalkyl, aminoalkyl, carboxyalkyl or mercaptoalkyl and where the carbon containing portions contain between 1 and 6 carbon atoms;

$X^4$ is selected from the group consisting of —CH$_2$, —CHOH, —C=O, —CHCH$_2$SH, or —CHCO$_2$H;

$Y^4$ is selected from the group consisting of —SH, or —NR$^{27}$R$^{28}$,

R$^{27}$ and R$^{28}$ being the same or different and are defined in the same manner as R$^{21}$ and R$^{26}$, respectively, and M$^2$ is selected from the group consisting of Technetium, Rhenium, Indium, Gallium, Cobalt, Copper, Yttrium, Terbium, Samarium, Holmium, Lutetium, Gadolinium, Manganese and Iron;

or the structure:

V where R$^{29}$ and R$^{30}$ are the same or different and each is selected from the group consisting of hydrogen, hydroxyl, carboxyl, amino, alkyl, aryl, alkaryl, alkaroyl, hydroxyalkyl, hydroxyalkaryl, alkoxy, alkoxycarbonyl and carbamoyl and where the carbon containing portions contain between 1 and 10 carbon atoms;

R$^{31}$ and R$^{32}$ are selected from the group consisting of hydrogen, alkyl, aryl, alkaryl, hydroxyalkyl and alkoxyalkyl;

R$^{33}$ is selected from the group consisting of hydrogen, alkyl, hydroxyalkyl, aminoalkyl, carboxyalkyl or mercaptoalkyl and where the carbon containing portions contain between 1 and 6 carbon atoms;

$X^5$ is selected from the group consisting of —CH$_2$, —CHOH, —C=O, —CHCH$_2$SH, or —CHCO$_2$H; and

$Y^5$ is selected from the group consisting of —SH, or —NR$^{34}$R$^{35}$, R$^{34}$ and R$^{35}$ being the same or different and are defined in the same manner as R$^{29}$ and R$^{32}$, respectively.

M$^3$ is selected from the group consisting of Technetium, Rhenium, Indium, Gallium, Cobalt, Copper, Yttrium, Terbium, Samarium, Holmium, Lutetium, Gadolinium, Manganese and Iron, and $Z^2$ is selected from the group consisting of —CH$_2$, —CHOH, and —C=O;

or the structure:

where $R^{36}$ and $R^{37}$ are the same or different and each is selected from the group consisting of hydrogen, hydroxyl, carboxyl, amino, alkyl, aryl, alkaryl, alkaroyl, hydroxyalkyl, hydroxyalkaryl, alkoxy, alkoxycarbonyl and carbamoyl and where the carbon containing portions contain between 1 and 10 carbon atoms;

$R^{38}$ and $R^{39}$ are selected from the group consisting of hydrogen, alkyl, aryl, alkaryl, hydroxyalkyl and alkoxyalkyl;

$R^{40}$ is selected from the group consisting of hydrogen, alkyl, hydroxyalkyl, aminoalkyl, carboxyalkyl or mercaptoalkyl and where the carbon containing portions contain between 1 and 6 carbon atoms;

$X^6$ is selected from the group consisting of $-CH_2$, $-CHOH$, $-C=O$, $-CHCH_2SH$, or $-CHCO_2H$; and $Y^6$ is selected from the group consisting of $-SH$, or $-NR^{41}R^{42}$, $R^{41}$ and $R^{42}$ being the same or different and are defined in the same manner as $R^{36}$ and $R^{40}$, respectively.

$M^4$ is selected from the group consisting of Technetium, Rhenium, Indium, Gallium, Cobalt, Copper, Yttrium, Terbium, Samarium, Holmium, Lutetium, Gadolinium, Manganese and Iron, and $Z^3$ is selected from the group consisting of $-CH_2$, $-CHOH$, and $-C=O$.

Also provided by the present invention is a method of using the radionuclide complex composition of the present invention by administering it to an individual, in a pharmacologically acceptable carrier, for imaging, diagnostic, or therapeutic purposes. The diagnostic method permits detecting the presence or absence of a biological tissue that has a particular steroid receptor associated therewith by administering a diagnostically effective amount of the radionuclide complex to an individual. The therapeutic method permits the delivery of a therapeutic amount of the radionuclide complex to a biological site that has a particular steroid receptor associated therewith by administering the complex to an individual.

Among the several advantages of the present invention include the provision of a radionuclide complex that mimics the molecular topology of asteroid molecule; a radionuclide complex that is capable of binding to a steroid receptor in a manner similar to a natural steroid molecule; a steroid-based radionuclide complex that is of a size to permit it to permeate cell and nuclear membranes so as to bind to steroid receptors in the nucleus of a cell; and a method for imaging or providing therapy to biological tissue containing steroid receptors utilizing a radionuclide-steroid complex. Other and further advantages of the inventions disclosed herein will become apparent to one of ordinary skill in the art. For instance, this internal bifunctional approach can be utilized to place a phosphorous atom at any site in the steroid skeleton. In this case, the adjacent atoms can be either carbon or heteroatoms such as oxygen, sulfur, or nitrogen.

DETAILED DESCRIPTION OF THE PREFERRED EMBODIMENTS

In accordance with the present invention, it has been discovered that at least one of the tetrahedral carbon centers of asteroid skeleton structure may be replaced by a metal ion provided that the adjacent centers are replaced by a suitable donor atom capable of bonding to a metal ion to provide a radionuclide complex. In the synthesis of such a complex, the metal ion can assume a tetrahedral or square-pyramidal geometry. In this manner, a radionuclide complex that mimics the steroid structure in molecular topology, size, and binding properties is provided. It has also been discovered that ligands useful in the preparation of radionuclide-steroid mimics may be provided which, upon complexation with the appropriate metal under the appropriate complexing conditions, form the radionuclide-steroid mimic compositions of this invention. Thus, radionuclide complexes that mimic the steroid perhydrocyclopentanophenanthrene ring structure (the steroid skeleton structure) are provided that have physical and biological characteristics, such as molecular topology, size and binding properties, that are similar to those of a non-modified steroid molecule.

Radionuclides prepared in accordance with the present invention can be used as radioimaging agents, radiotherapeutic agents, or as prognostication tools for analysis of disease states. It is known that steroid receptors are found in some tumor cells, particularly breast cancer and prostate cancer cells, and that an association between the presence of steroid receptors and the cancer exists. As a result, the radionuclide steroid mimics of the present invention find particular use in radioimaging, radiotherapy or as an aid in the prognostication of the state of a tumor or other biological tissue that has steroid receptors associated therewith. It is believed that the steroid-based radionuclides or "mimics" are likely to provide more consistent results because of the similarity of the structure to the natural steroid molecule and the increased likelihood that specific binding will occur.

A typical steroid molecule consists of a perhydrocyclopentanophenanthrene ring structure and may be either an aliphatic or an aromatic steroid. These general structures are hereinafter referred to as the "steroid skeleton structure" and are illustrated below as structures VII and VIII, respectively:

Using the standard nomenclature and numbering system adopted for use in the steroid ring structure, the carbon centers at positions 5, 8, 9, 14, and 17 in structure VII, and the carbon centers at positions 8, 9, 14 and 17 in structure VIII are regarded as tertiary centers and the carbon centers at positions 10 and 13 in structure VII and position 13 in structure VIII are regarded as quaternary centers. In a preferred embodiment of the present invention, a selected metal ion is positioned at one of the tertiary or quaternary centers of the steroid structure and donor atoms, heteroatoms capable of bonding to the metal ion, are positioned at the carbon centers adjacent to the position located by the metal ion in place of the carbon atoms. The donor atoms preferably contain a thiol, amide, carboxylate or an amine group. In particular, the donor atoms adjacent to the selected position of the metal ion will provide an $N_3S$ or $N_2S_2$ chelating core in order to satisfy the valency of the metal ion like technetium, rhenium, and gallium. It is also possible to incorporate the metal ions at the secondary centers in the steroid skeleton, but it is preferred to utilize the tertiary and quaternary centers.

In preferred embodiments, the radionuclide complex of the present invention will have one of the following schematic structures (IX–XIX):

IX

X

XI

XII

XIII

XIV

XV

XVI

XVII

XIX where M is a metal ion and X, Y and W are donor atoms capable of bonding to the metal ion and forming a radionuclide complex. It is of course understood that other reactive moieties or ligands may be required to satisfy the valency of the metal ion in the above schematic structures to provide a stable metal complex and that various sidechains may be presented at any of the remaining carbon centers of the steroid skeleton for particular steroid structures. For example, the steroid mimic ligands described above provide four donor atoms and for metals having additional sites, these could be filled by water, hydroxide, chloride atoms or other ligands.

The metal ion incorporated into the steroid skeleton structure can be any metal ion that is useful in therapy, imaging, or for the prognosis of disease. Preferably, radioactive isotopes of metals are used for diagnostic imaging, and therapeutic applications, but non-radioactive metal ions can be used for MRI and X-ray diagnostic procedures. For diagnostic radio-pharmaceuticals, useful radionuclide metals include, but are not limited to gamma-emitting nuclides such as, Tc-99m, In-111, Tl-201, Co-57, Cu-67; Ga-67 and Re-186. Useful therapeutic radionuclide metals include, but are not limited to beta and/or alpha emitting nuclides such as, Yt-90, Sr-89, Sm-153, Ho-166, Re-186, Re-188, Pb-212 and Tb-161. Useful diagnostic metals for MRI and/or X-ray contrast media include, but ar not limited to Gd, Mn, Fe, Dy, Bi, W and Pb. A list of radionuclides can be found in the text "Table of Isotopes," Seventh Edition (ed. Lederer and Shirley, John Wiley and Sons, Inc.) the entirety of which is herein incorporated by reference hereto.

Ligands useful in the preparation of the radionuclide complexes of this invention are prepared as a precursor to the radionuclide complexes and are useful compositions. The ligands are useful in the preparation of the radionuclide complexes in that the ligand is typically provided separate from the radionuclide for commercial use. Therefore, the ligands of this invention are useful as a component of kits for producing radionuclide complexes. The radionuclide containing solution may be obtained from radionuclide generators in a known manner. For example, when forming a technetium complex, a pertechnate solution may be obtained from a technetium generator in a known manner. The radionuclide complex forming reaction is then carried out under appropriate reaction conditions. For example, the technetium 99m complex forming reaction is carried out under technetium complex forming temperatures, e.g. 20° C. to about 100° C. for 10 minutes to several hours. An excess of the appropriate ligand over the radionuclide complex forming amounts is generally used. Thus, provided by the present invention are ligands of the following structures: (I, II, XXV-XXVII)

The above ligands are complexed with the selected metal to form a radionuclide complex having one of the structures IX–XIX, as shown above. The formation of radionuclide complexes is well known to those skilled in the art.

Figure 1:
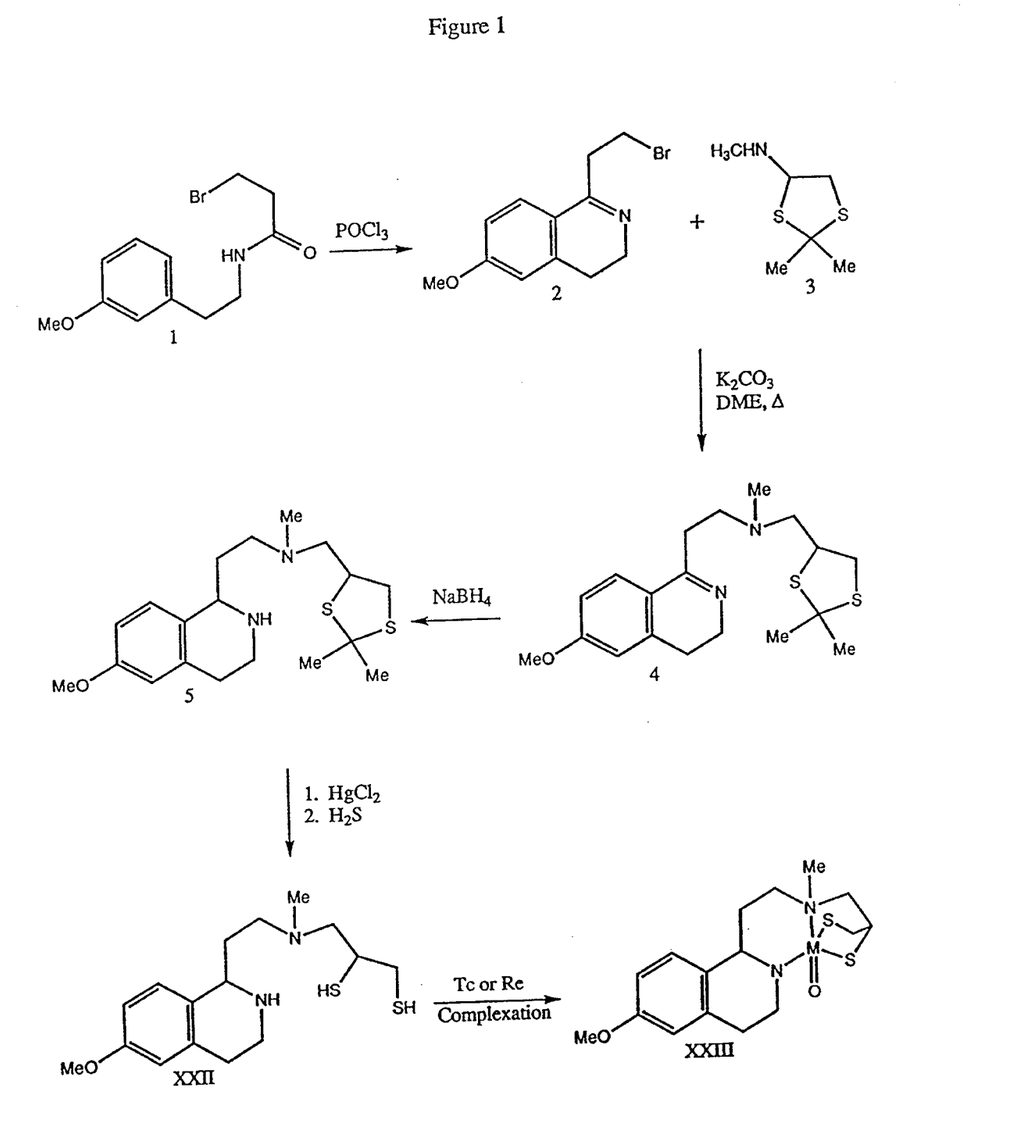
FIGS. 1 and 2 depict chemical synthesis protocols that may be used to prepare certain compounds of the present invention.
Figure 2:
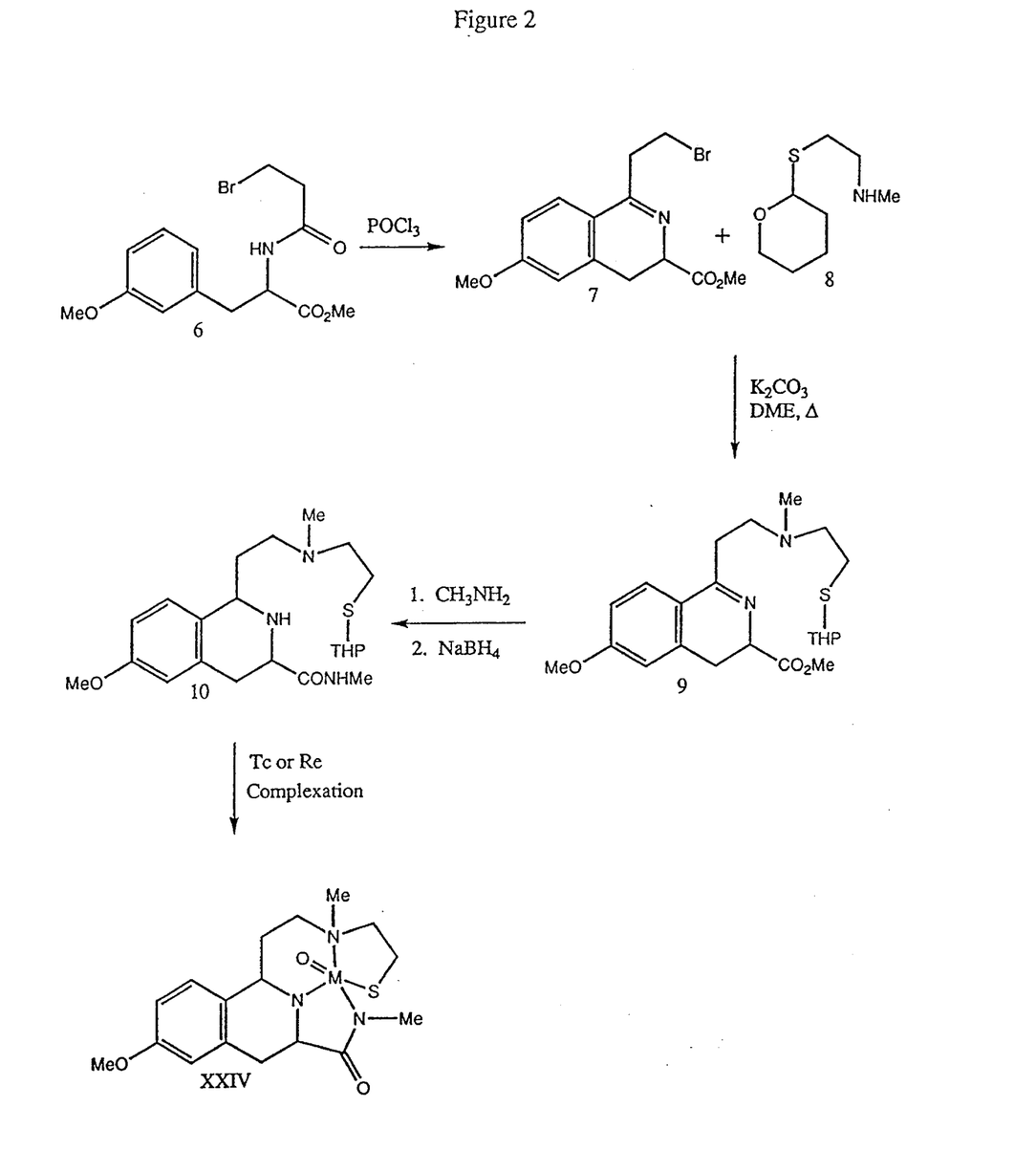

A schematic diagram of the synthesis of two exemplary $N_2S_2$ and $N_3S$ metal based steroid mimics are shown in FIGS. 1 and 2, respectively. The starting materials, i.e. compounds 1, 3, 6 and 8, can be prepared by standard functional group transformations from commercially available chemicals, i.e. 3-methoxyphenethylamine, 3-hydroxyphenylalanine, 2,3-dimercapotopropanol, and mercaptoethylamine.

Preparation of the dihydroisoquinoline derivatives 2 or 7 is accomplished via the known Bischler-Napieralski reaction (T. R. Govindachari et al., Organic Reactions, Volume 6). Alternatively, the tetrahydroisoquioline derivatives can be prepared by the Pictet-Spengler procedure using appropriate β-phenethylamine derivatives and aldehydes. The key step in the synthesis is the alkylation of the amines 3 or 8 with the bromides 2 or 7. Subsequent steps are routine and standard functional group transformations.

In a preferred embodiment of the ligand having structure I, $R^1$ is —OH or —OCH$_3$; $R^2$ is —H or —COCH$_3$; $R^3$ is —CH$_3$; $R^4$ is —CH$_2$SH; $R^5$ is —H; $X^1$ is —CH$_2$ or —C=O; and $Y^1$ is —SH or —NHCOCH$_3$. In a preferred embodiment of the ligand having structure II, $R^8$ is —OH or —OCH$_3$; $R^9$ is —H or —COCH$_3$; $R^{10}$ is —CH$_3$; $R^{11}$ is —CH$_2$SH; $R^{12}$ is —H; $X^2$ is —CH$_2$ or —C=O; $Y^2$ is —SH or —NHCOCH$_3$; and $Z^1$ is —CHOH or —C=O. In a preferred embodiment of the metal complex of structure III, $R^{15}$ is —OH or —OCH$_3$; $R^{16}$ is —H or —COCH$_3$; $R^{17}$ is —CH$_3$; $R^{18}$ is —CH$_2$S$^{-1}$; $R^{19}$ is —H; $X^3$ is —CH$_2$ or —C=O; and $Y^3$ is —S$^-$ or —NCOCH$_3$. In a preferred embodiment of the metal complex having structure IV, $R^{22}$ is —OH or —OCH$_3$; $R^{23}$ is —H or —COCH$_3$; $R^{24}$ is —CH$_3$; $R^{25}$ and $R^{26}$ are —H; $X^4$ is —CH$_2$S$^-$; and $Y^4$ is —S$^-$ or —NCOCH$_3$. In a preferred embodiment of the metal complex having structure V, $R^{29}$ is —OH or —OCH$_3$; $R^{30}$ is —H or —COCH$_3$; $R^{31}$ is —CH$_3$; $R^{32}$ is —CH$_2$S$^-$; $R^{33}$ is —H; $X^5$ is —CH$_2$ or —C=O; $Y^5$ is —S$^-$ or —NCOCH$_3$; and $Z^2$ is —CHOH or —C=O. In a preferred embodiment of the metal complex having structure VI, $R^{36}$ is —OH or —OCH$_3$; $R^{37}$ is —H or —COCH$_3$; $R^{38}$ is —CH$_3$; $R^{39}$ and $R^{40}$ are —H; $X^6$ is —CH$_2$S$^-$; and $Y^6$ is —S$^-$ or —NCOCH$_3$; and $Z^3$ is —CHOH or —C=O.

The labelling of ligands can be accomplished even with the protecting groups intact. It is known that thioketals and hemithioketals are cleaved under acidic conditions using heavy metal ions such as mercury or silver (T. Greene, Protective Groups in Organic Synthesis, J. Wiley: New York, 1991). It has been shown that the S-tetrahydropyranyl(s-THP) group containing N3S ligands undergo efficient labelling with Tc and Re without prior removal of the protecting group (Srinivasan, et al., U.S. Pat. No. 5,021,556). It has also been demonstrated that the S-THP group is efficiently removed under neutral and mildly alkaline conditions. Thus, the protected ligands 7 and 13 may be used without prior removal of the protecting groups.

Two particularly useful steroid mimics are those that mimic the steroids cortisone and estradiol. When prepared in accordance with the methods described herein, the following structures, XXVIII and XXIX, represent the structure of two radionuclide complexes that will serve as cortisone and estradiol mimics:

In use, the radionuclide complexes of the present invention may be used for diagnostic and therapeutic purposes. The diagnostic method may be used to detect the presence or absence of a target site within an individual. The method comprises the steps of administering to an individual a diagnostically effective dose of one of the radionuclide complexes described above, where the metal or metal oxide is a radionuclide and the steroid mimic is capable of binding to a steroid receptor on the target site. This step is followed by a step of detecting the biodistribution of the radionuclide in the individual to determine the presence or absence of the target site in the host.

The amount of the diagnostic agent according to the present invention should be sufficient to provide satisfactory imaging. For example, when using an aqueous solution, the dosage is generally from about 1 to about 50 mCi, and more preferrably from about 10 to about 30 mCi. The diagnostic agent should be administered so as to remain in the patient for about 1 to 3 hours, although both longer and shorter time periods are acceptable. Therefore, convenient ampules containing 1 to 10 ml of aqueous solution may be prepared. Of course, the precise dose for diagnostic purposes is dependent upon the particular radionuclide complex used and its affinity for its corresponding receptors. The diagnostic agent may be administerd by various means including, intravenous and intratumoral administration. Preferred radionuclides are Tc-99m and Re-186.

The therapeutic method may be used to deliver the radionuclide complex to a target site in the individual. The method comprises the step of administering to an individual a therapeutically effective dose of one of the radionuclide complexes described above, where the metal is an alpha or beta emitting metal or metal oxide and the steroid mimic is capable of binding to the target site. A therapeutically effective dose is generally from about 20 mCi to about 300 mCi. One of ordinary skill in the art is able to determine the precise dose by taking into consideration the discussion above with respect to dosage. Preferred radionuclides are Re-186, Re-188, Cu-67, Rh-105, Au-198, Au-199, and Bi-212.

The following examples describe preferred embodiments of the invention. Other embodiments within the scope of the claims herein will be apparent to one skilled in the art from consideration of the specification or practice of the invention as described herein. It is intended that the specification, together with the following examples, be considered exemplary only, with the scope and spirit of the invention being indicated by the claims which follow these examples.

EXAMPLE 1

This example illustrates the synthesis and preparation of a ligand having the structure:

This synthesis is shown schematically in FIG. 1. A mixture of 3-bromo-N-[β-(3-methoxy)phenethyl]propionamide (3.3 g, 10 mmol) and phosphorous oxychloride (1.7 g, 11 mmol) in 1,2-dichloroethane (20 mL) was heated under reflux for 6 hours. The reaction mixture was cooled, treated with saturated sodium bicarbonate solution (20 mL), and stirred at ambient temperature for 30 minutes. The organic layer was separated, dried ($MgSO_4$), filtered, and the filtrate taken to dryness under reduced pressure. The residue was purified by chromatography over silica gel (100 g). Elution with chloroform afforded the desired bromide 1 as pale reddish yellow gum.

A mixture of the bromide 1(3.2 g, 10 mmol), the amine 3(1.0 g, 10 mmol), finely ground anhydrous potassium carbonate (1.5 g, 11 mmol), and sodium iodide (0.3 g, 2 mmol) in dry glyme (25 mL) is heated under reflux for 4 hours. The reaction mixture is filtered and the filtrate taken to dryness under reduced pressure. The residue is then chromotographed over silica gel (150 g) to furnish the thioketal 4.

A solution of the thioketal-imine 4(4.0 g, 10 mmol) in ethanol (20 mL) is treated with sodium borohydride (0.4 g, 11 mmol) and stirred at ambient temperature for 12 hours. The reaction mixture is poured onto water and extracted with methylene chloride (3×25 mL). The combined organic extracts are then dried ($Na_2SO_4$), filtered, and the filtrate taken to dryness under reduced pressure. The residue is then chromatographed over silica gel (150 g) to furnish the desired product 5.

A mixture of tetrahydroisoguinoline 5 (3.3 g, 10 mmol) and mercuric chloride (2.9 g, 11 mmol) in methanol (25 mL) is stirred at ambient temperature for 2 hours. Thereafter, $H_2S$ gas is bubbled through the solution for 15 minutes to precipitate mercuric sulfide. The mixture is filtered through Celite and the filtrate taken to dryness under reduced pressure to give the dithiol XXII. Due to air-sensitivity of dithiols, it is preferable to use this material immediately.

EXAMPLE 2

This example illustrates the preparation of a Tc-99m based steroid mimic from the ligand having structure XXII described in Example 1. The formation of this radionuclide complex is also shown in FIG. 1.

A mixture of the ligand XXII (1 mg), 0.01N sodium hydroxide solution (0.1 mL), and ethanol (0.9 mL) is treated with technetium tartarate solution (0.2 mL). The entire mixture is heated at 100° C. for 15 minutes. The reaction mixture is cooled to ambient temperature and the resulting mixture is purified by reverse phase (C-18) HPLC to obtain the derived complex XXIII where M is Tc.

EXAMPLE 3

This example illustrates the preparation of a rhenium-186 based steroid mimic from the ligand having strucutre XXII described in Example 1.

A mixture of the ligand (200 Mg) and citric acid (50 Mg), stannous chloride (20 Mg) and sodium perhenate solution (0.5 mL) is heated at 100° C. for 15 minutes. The reaction mixture is cooled to ambient temperature and the resulting solution is purified by reverse phase (C-18) HPLC to obtain the desired rhenium complex XXIII wherein M is Re.

EXAMPLE 4

This example illustrates the synthesis and preparation of a ligand having structure:

The synthesis of this ligand is shown schematically in FIG. 2.

A mixture of 3-bromo-N[1-(3-methoxy)-2-carbomethoxy)phenethyl]propionamide 6 (3.9 g 10 mmol) and phosphorous trichloride (1.7 g, 11 mmol) in 1,2-dichloroethane (20 mL) is heated under reflux for 6 hours. The reaction mixture is cooled, treated with saturated sodium bicarbonate solution (20 mL), and stirred at ambient temperature for 30 minutes. The organic layer is separated, dried, (MgSO$_4$), filtered, and the filtrate taken to dryness under reduced pressure. The residue is purified by silica gel chromatography to give the derived bromide 7.

A mixture of the bromide 7 (3.3 g, 10 mmol), the amine 8(1.8 g, 11 mmol), finely ground anhydrous potassium carbonate (1.5 g, 11 mmol), and sodium iodide (10.3 g, 2 mmol) in dry glyme (25 mL) is heated under reflux for 4 hours. The reaction mixture is filtered and the filtrate taken to dryness under reduced pressure. The residue is purified by chromatography over silica gel (150 g) to furnish the thioketal 9.

A solution of the thioether-imine 9(4.2 g, 10 mmol) in ethanol (20 mL) is treated with sodium borohydride (0.4 g, 11 mmol) and stirred at ambient temperature for 12 hours. The reaction mixture is poured onto water and extracted with methylene chloride (3×25 mL). The combined organic extracts are then dried (Na$_2$SO$_4$), filtered and the filtrate taken to dryness under reduced pressure. The residue is purified by chromatography over silica gel (150 g) to give the desired S-protected ligand having structure 10. There is no need to deprotect the THP group since this is often removed during the labelling (metal complexation) process.

EXAMPLE 5

This example illustrates the preparation of a Tc-99m based steroid mimic from the ligand having structure 10 described in Example 4. This synthesis is also shown schematically in FIG. 2.

A solution of the ligand 10(1 mg), in ethanol (0.7 mL) was treated with 0.3 mL of pH 6 acetate buffer and 0.2 mL of technetiumtartarate solution. The entire mixture is heated under inert atmosphere for 15 minutes, cooled to ambient temperature, and purified by reverse phase (C-18) HPLC to give the desired complex XXIV where M is Tc.

EXAMPLE 6

This example illustrates the preparation of a rhenium-186 based steroid mimic from the ligand having the structure 10 described in Example 4.

A mixture of the ligand 10 (200 Mg), citric acid (50 Mg) stannous chloride (20 Mg) and sodium perrhenate solution (0.5 mL) is heated under inert atmosphere for 15 minutes, cooled to ambient temperature, and purified by reverse phrase (C-18) HPLC to furnish the desired complex XXIV where M is Re.

EXAMPLE 7

This example illustrates a protocol by which ligands useful in the preparation of steroid-based radionuclide complexes may be synthesized where the metal ion is located at positions 9, 8 and 13 in the steroid skeleton structure. The ligands for the preparation of radionuclide complexes having structures XV, XVI, and XVII, as described above, are shown below as structures XXV, XXVI, and XXVII:

These ligands may be prepared as shown below by the assembly of key intermediates determined by a retrosynthetic analysis of the respective radionuclide complexes. All of the retrosynthetically derived fragments can be prepared from readily available or known starting materials and can be combined to yield the desired ligand using known reactions and reaction conditions.

In the preparation of the ligand having structure XXV, the following compounds derived as retrosynthetic fragments of the ligand can be prepared and combined to yield the ligand:

For example, compound 11 can be prepared from 2-hydroxymethyl-4-methoxypyridine and compound 13 can be prepared from methyl 2-cyclopentanonecarboxylate and where R is selected from the group consisting of hydrogen, hydroxyl, carboxyl, amino, alkyl, aryl, alkaryl, alkaroyl, hyfroxyalkyl, hydroxyalkaroyl, alkoxy, alkoxycarbonyl and carbamoyl and where the carbon containing portions contain between 1 and 10 carbon atoms.

The preparation of a ligand which can be complexed with a metal ion to place the metal at position 8 would require the synthesis of the ligand having structure XXVI. The retrosynthetic analysis of the ligand yields three fragments as set forth below:

Compound 14 can be prepared from 3-methoxybenzamide and compound 15 can be prepared from proline where R is as defined above.

The preparation of a ligand useful in the preparation of a radionuclide complex which places the metal ion at position 13 would require the synthesis of a ligand having structure XXVII. The retrosynthetic analysis of this ligand yields two fragments of which 16 is commercially available (N-acetyl-homocysteine thiolactone). Compound 17 cam be prepared from 1-cyano-3,4-dihydro-6-methoxynaphthalene (S. Amin et al., 1981 J. Org. Chem. 46, 2394).

What is claimed is:

1. A ligand having the structure:

where $R^1$ and $R^2$ are the same or different and each is selected from the group consisting of hydrogen, hydroxyl, carboxyl, amino, alkyl, aryl, alkaryl, alkaroyl, hydroxyalkyl, hydroxyalkaroyl, alkoxy, alkoxycarbonoyl and carbamoyl and where the carbon containing portions of $R^1$ and $R^2$ contain between 1 and 10 carbon atoms; $R^3$, $R^4$ and $R^5$ are the same or different and each is selected from the group consisting of hydrogen, alkyl, hydroxyalkyl, aminoalkyl, carboxyalkyl and mercaptoalkyl and where the carbon containing portions of $R^3$, $R^4$ and $R^5$ contain between 1 and 6 carbon atoms; $X^1$ is selected from the group consisting of —$CH_2$, —CHOH, —C=O, —$CHCH_2SH$, and —$CHCO_2H$; and $Y^1$ is selected from the group consisting of —SH, and —$NR^6R^7$, $R^6$ and $R^7$ being the same or different and are defined in the same manner as $R^1$ and $R^3$, respectively.

2. The ligand of claim 1 wherein $R^1$ is —OH or —$OCH_3$; $R^2$ is —H or —$COCH_3$; $R^3$ is —$CH_3$; $R^4$ is —$CH_2SH$; $R^5$ is —H; $X^1$ is —$CH_2$ or —C=O; and $Y^1$ is —SH or —$NHCOCH_3$.

3. A ligand having the structure:

where $R^8$ and $R^9$ are the same or different and each is selected from the group consisting of hydrogen, hydroxyl, carboxyl, amino, alkyl, aryl, alkaryl, alkaroyl, hydroxyalkyl, hydroxyalkyl, alkoxy, alkoxycarbonyl and carbamoyl and where the carbon containing portions of $R^8$ and $R^9$ contain between 1 and 10 carbon atoms; $R^{10}$, $R^{11}$, and $R^{12}$ are the same or different and each is selected from the group consisting of hydrogen, alkyl, hydroxyalkyl, aminoalkyl, carboxyalkyl and mercaptoalkyl and where the carbon containing portions of $R^{10}$, $R^{11}$, and $R^{12}$ contain between 1 and 6 carbon atoms; $X^2$ is selected from the group consisting of —$CH_2$, —CHOH, —C=O, —$CHCH_2SH$, or —$CHCO_2$; $Y^2$ is selected from the group consisting of —SH and —$NR^{13}R^{14}$, $R^{13}$ and $R^{14}$ being the same or different and are defined in the same manner as $R^8$ and $R^{10}$, respectively; and $Z^1$ is selected from the group consisting of —$CH_2$, —CHOH, and —C=O.

4. The ligand of claim 3, wherein $R^8$ is —OH or —$OCH_3$; $R^9$ is —H or —$COCH_3$; $R^{10}$ is —$CH_3$; $R^{11}$ is —$CH_2SH$; $R^{12}$ is —H; $X^2$ is —$CH_2$ or —C=O; $Y^2$ is —SH or —$NHCOCH_3$; and $Z^1$ is —CHOH or —C=O.

5. A complex having the structure:

where $R^{15}$ and $R^{16}$ are the same or different and each is selected from the group consisting of hydrogen, hydroxyl, carboxyl, amino, alkyl, aryl, alkaryl, alkaroyl, hydroxyalkyl, hydroxyalkyl, alkoxy, alkoxycarbonyl and carbamoyl and where the carbon containing portions of $R^{15}$ and $R^{16}$ contain between 1 and 10 carbon atoms; $R^{17}$ is selected from the group consisting of hydrogen, aklyl, aryl, alkaryl, hydroxyalkyl, mercaptoalkyl, and alkoxyalkyl; $R^{18}$ and $R^{19}$ are the same or different and each is selected from the group consisting of hydrogen, alkyl, hydroxyalkyl, aminoalkyl, carboxyalkyl and mercaptoalkyl and where the carbon containing portions of $R^{18}$ and $R^{19}$ contain between 1 and 6 carbon atoms; $X^3$ is selected from the group consisting of —$CH_2$, —CHOH, —C=O, —$CHCH_2SH$, and —$CHCO_2H$; $Y^3$ is selected from the group consisting of —S— and —$NR^{20}R^{21}$, where $R^{20}$ and $R^{21}$ are defined in the same manner as $R^{15}$ and $R^{16}$, respectively; and $M^1$ is selected from the group consisting of Technetium, Rhenium, Indium, Gallium, Cobalt, Copper, Yttrium, Terbium, Samarium, Holmium, Lutetium, Gadolinium, Manganese and Iron.

6. The complex as set forth in claim 5 wherein the metal ion is a radionuclide.

7. The complex as set forth in claim 6 wherein $R^{15}$ is —OH or —OCH$_3$; $R^{16}$ is —H or —COCH$_3$; $R^{17}$ is —CH$_3$; $R^{18}$ is —CH$_2$S—; $R^{19}$ is —H; $X^3$ is —CH$_2$ or —C=O; and $Y^3$ is —S$^-$ or —NCOCH$_3$.

8. A complex having the structure:

IV where $R^{22}$ and $R^{23}$ are the same or different and each is selected from the group consisting of hydrogen, hydroxyl, carboxyl, amino, alkyl, aryl, alkaryl, alkaroyl, hydroxyalkyl, hydroxyalkaryl, alkoxy, alkoxycarbonyl and carbamoyl and where the carbon containing portions of $R^{22}$ and $R^{23}$ contain between 1 and 10 carbon atoms; $R^{24}$ and $R^{25}$ is selected from the group consisting of hydrogen, alkyl, aryl, alkaryl, hydroxyalkyl and alkoxyalkyl; $R^{26}$ is selected from the group consisting off hydrogen, alkyl, hydroxyalkyl, aminoalkyl, carboxyalkyl and mercaptoalkyl and where the carbon containing portions of $R^{24}$, $R^{25}$ and $R^{26}$ contain between 1 and 6 carbon atoms; $X^4$ is selected from the group consisting of —CH$_2$, —CHOH, —C=O, —CHCH$_2$SH, and —CHCO$_2$H; $Y^4$ is selected from the group consisting of —SH, and —NR$^{27}$R$^{28}$, $R^{27}$ and $R^{28}$ being the same or different and are defined in the same manner as $R^{21}$ and $R^{26}$, respectively, and $M^2$ is selected from the group consisting of Technetium, Rhenium, Indium, Gallium, Cobalt, Copper, Yttrium, Terbium, Samarium, Holmium, Lutetium, Gadolinium, Manganese and Iron.

9. The complex as set forth in claim 8 wherein the metal ion is a radionuclide.

10. The complex as set forth in claim 9 wherein $R^{22}$ is —OH or —OCH$_3$; $R^{23}$ is —H or —COCH$_3$; $R^{24}$ is —CH$_3$; $R^{25}$ and $R^{26}$ are —H; $X^4$ is —CH$_2$S; and $Y^4$ is —S$^-$ or —NCOCH$_3$.

11. A complex having the structure:

V where $R^{29}$ and $R^{30}$ are the same or different and each is selected from the group consisting of hydrogen, hydroxyl, carboxyl, amino, alkyl, aryl, alkaryl, alkaroyl, hydroxyalkyl, hydroxyalkaryl, alkoxy, alkoxycarbonyl and carbamoyl and where the carbon containing portions of $R^{29}$ and $R^{30}$ contain between 1 and 10 carbon atoms; $R^{31}$ and $R^{32}$ are selected from the group consisting of hydrogen, alkyl, aryl, alkaryl, hydroxyalkyl and alkoxyalkyl; $R^{33}$ is selected from the group consisting of hydrogen, alkyl, hydroxyalkyl, aminoalkyl, carboxyalkyl and mercaptoalkyl and where the carbon containing portions of $R^{31}$ and $R^{32}$ contain between 1 and 6 carbon atoms; $X^5$ is selected from the group consisting of —CH$_2$, —CHOH, —C=O, —CHCH$_2$SH, and —CHCO$_2$H; and $Y^5$ is selected from the group consisting of —SH, and —NR$^{34}$R$^{35}$, $R^{34}$ and $R^{35}$ being the same or different and are defined in the same manner as $R^{29}$ and $R^{32}$, respectively; and $M^3$ is selected from the group consisting of Technetium, Rhenium, Indium, Gallium, Cobalt, Copper, Yttrium, Terbium, Samarium, Holmium, Lutetium, Gadolinium, Manganese and Iron, and $Z^2$ is selected from the group consisting of —CH$_2$, —CHOH, and —C=O.

12. The complex as set forth in claim 11 wherein the metal ion is a radionuclide.

13. The complex as set forth in claim 12 wherein $R^{29}$ is —OH or —OCH$_3$; $R^{30}$ is —H or —COCH$_3$; $R^{31}$ is —CH$_3$; $R^{32}$ is —CH$_2$S$^-$; $R^{33}$ is —H; $X^5$ is —CH$_2$ or —C=O; $Y^5$ is —S$^-$ or —NCOCH$_3$; and $Z^2$ is —CHOH or —C=O.

14. A complex having the structure:

VI where $R^{36}$ and $R^{37}$ are the same or different and each is selected from the group consisting of hydrogen, hydroxyl, carboxyl, amino, alkyl, aryl, alkaryl, alkaroyl, hydroxyalkyl, hydroxyalkaryl, alkoxy, alkoxycarbonyl and carbamoyl and where the carbon containing portions of $R^{36}$ and $R^{37}$ contain between 1 and 10 carbon atoms; $R^{38}$ and $R^{39}$ are selected from the group consisting of hydrogen, alkyl, aryl, alkaryl, hydroxyalkyl and alkoxyalkyl; $R^{40}$ is selected from the group consisting of hydrogen, alkyl, hydroxyalkyl, aminoalkyl, carboxyalkyl and mercaptoalkyl and where the carbon containing portions of $R^{38}$ and $R^{39}$ contain between 1 and 6 carbon atoms; $X^6$ is selected from the group consisting of —CH$_2$, —CHOH, —C=O, —CHCH$_2$SH, and —CHCO$_2$H; and $Y^6$ is selected from the group consisting of —SH, and —NR$^{41}$R$^{42}$, $R^{41}$ and $R^{42}$ being the same or different and are defined in the same manner as $R^{36}$ and $R^{40}$, respectively; and $M^4$ is selected from the group consisting of Technetium, Rhenium, Indium, Gallium, Cobalt, Copper, Yttrium, Terbium; Samarium, Holmium, Lutetium, Gadolinium, Manganese and Iron, and $Z^3$ is selected from the group consisting of —CH$_2$, —CHOH, and —C=O.

15. The complex as set forth in claim 14 wherein the metal ion is a radionuclide.

16. The complex as set forth in claim 15 wherein $R^{36}$ is —OH or —OCH$_3$; $R^{37}$ is —H or —COCH$_3$; $R^{38}$ is —CH$_3$; $R^{39}$ and $R^{40}$ are —H; $X^6$ is —CH$_2$S; and $Y^6$ is —S$^-$ or —NCOCH$_3$; and $Z^3$ is —CHOH or —C=O.

\* \* \* \* \*